United States Patent [19]

Gilbert

[11] 4,245,129

[45] Jan. 13, 1981

[54] PROCESS FOR PREPARING HEXANITROBIBENZYL

[75] Inventor: Everett E. Gilbert, Morristown, N.J.

[73] Assignee: The United States of America as represented by the Secretary of the Army, Washington, D.C.

[21] Appl. No.: 66,599

[22] Filed: Aug. 14, 1979

[51] Int. Cl.³ .............................................. C07C 79/10
[52] U.S. Cl. ..................................................... 568/931
[58] Field of Search ......................................... 568/931

[56] References Cited

U.S. PATENT DOCUMENTS 4,085,152   4/1978   Saiter et al. ........................... 568/931

*Primary Examiner*—Leland A. Sebastian
*Attorney, Agent, or Firm*—Nathan Edelberg; Robert P. Gibson; A. Victor Erkkila

[57] ABSTRACT

2,2',4,4',6,6'-hexanitrobibenzyl, an intermediate compound used for making hexanitrostilbene, is prepared by adding an aqueous alkaline metal hypochlorite solution containing an alkaline metal hydroxide to trinitrotoluene dispersed in a single solvent selected from the group consisting of methanol, ethanol, 2-methoxyethanol, isopropanol, acetone, tetrahydrofuran, N,N-dimethylformamide, N,N-dimethylacetamide, pyridine and N-methyl pyrrolidinone. The compound is then separated from the reaction mixture.

9 Claims, No Drawings

PROCESS FOR PREPARING HEXANITROBIBENZYL

GOVERNMENTAL INTEREST

The invention described herein may be manufactured, used and licensed by or for the Government for Governmental purposes without the payment to me of any royalties thereon.

BACKGROUND OF THE INVENTION

The present invention relates to a novel process for the preparation of 2,2',4,4',6,6'-hexanitrobibenzyl (HNB). This compound can be converted by various procedures to 2,2',4,4',6,6'-hexanitrostilbene, an important thermally-stable explosive which is also useful as a nucleating agent promoting a desired mode of crystallization of trinitrotoluene.

Prior to the present invention, the preferred method for preparing HNB was described in U.S. Pat. No. 3,505,413 and in a paper by Shipp and Kaplan, *Journal of Organic Chemistry*, 31, 857 (1966). The references teach dissolving TNT in one part tetrahydrofuran and two parts methanol by volume. A solution of sodium hypochlorite, which is made alkaline by the addition of sodium hydroxide, is then slowly added to the solution of TNT. During the addition of the sodium hypochlorite to the solution of TNT, the temperature did not exceed 35° C. After a suitable aging period (15 minutes), the crystalline material was filtered and then washed with methanol and dried. It is reported that the amount of HNB obtained is 79% of theoretical.

The prior art processes, while effective, do have a decided disadvantage in requiring the use of large volumes of solvent mixtures, which include expensive compounds. The U.S. Pat. No. 3,505,413 explains that the solvent should be one which will dissolve TNT at ambient temperatures and below and which, with the addition of a lower aliphatic alcohol, will provide a homogenous solution with an alkaline metal hypochlorite. Examples of such solvents are tetrahydrofuran, p-dioxane, diglyme and acetonitrile, which are all water-miscible materials.

Also, in accordance with the prior art process, the temperature at which the reaction proceeds must be kept low in order to minimize undesired side reactions between TNT and alkali as well as the competing reaction of the solvent system. The Shipp et al. paper suggests temperatures under 15° C.

In my co-pending application filed Sept. 26, 1979 Ser. No. 79,128, directed to the preparation of HNB, a solvent system is disclosed which utilizes a water-immiscible solvent and an aliphatic alcohol. While this system has a decided advantage over the Shipp, Kaplan process, it still requires a dual solvent with additional expense and handling.

SUMMARY OF THE INVENTION

Accordingly, an object of the present invention is to provide a process for producing HNB by dissolving TNT in a monosolvent system and then reacting the dissolved TNT with an alkaline metal hypochlorite.

Another object of the instant invention is to be able to allow the reaction to proceed without maintaining low temperatures.

These and other objects and advantages will be apparent in the detailed description to follow.

In the practice of the present invention, TNT, a compound well known in the art, is dissolved in a single solvent as opposed to a solvent system requiring a solvent, such as tetrahydrofuran, in mixture with a substantial amount of an aliphatic alcohol. Although throughout the application the terms 'dissolved' and 'solution' will be used, it should be recognized that the terms are also meant to include situations when the TNT is not completely dissolved but merely thoroughly dispersed throughout the solvent material.

DETAILED DESCRIPTION OF THE INVENTION

In the practice of the present invention, TNT, a compound well known in the art, is dissolved in a mono-solvent system as opposed to a mixture of a water-miscible or water-immiscible solvent and an aliphatic alcohol.

The solvents which can be employed in the present invention are methanol, ethanol, 2-methoxyethanol, isopropanol, acetone, tetrahydrofuran, N,N-dimethylformamide, N,N-dimethylacetamide, pyridine and N-methyl pyrrolidinone. While it is not completely understood why TNT dissolved in one of the aforesaid solvents permits the reaction to proceed, it apparently is not totally due to the solubility of TNT in the solvent. For example, the preferred solvent in the present process in methanol, which is readily available at low cost. However, the use of methanol alone would not appear promising in view of the work done by others. Shipp and Kaplan found it necessary to use a mixture of THF and methanol to obtain their results. While there does not appear to be published data on the solubility of TNT in methanol, the solubility of TNT in ethanol is reported as 2.85 grams of TNT per 100 grams of ethanol at 40° C. Accordingly, this would discourage the use of methanol as a solvent in the present reaction especially since the solubility would be further reduced by the addition of aqueous hypochlorite. Yet when methanol is used as the sole solvent, the reaction proceeds quite well with yields comparable to what is obtained with a dual solvent system.

It will be noted that each of the solvents disclosed for use in the instant process will not react preferentially with an alkaline metal hypochlorite. The amount of solvent used per gram of TNT can range from about 5 mils to about 20 mils although less than 5 mils and more than 20 mils solvent can be employed. Thus, significantly less solvent is necessary than in the Ship and Kaplan process where 15 mils of solvent per gram of TNT is employed.

The increase the solubility and increase the rate in which the TNT will go into solution, the solvent is heated to temperatures from about 40° C. to about 70° C. This can be done prior to or after adding the TNT. The temperature may also be adjusted after the reaction begins by utilizing the heat of reaction to raise the temperature. After the TNT is in solution or thoroughly dispersed, a dilute aqueous solution of metal hypochlorite made alkaline by the addition of an alkali metal hydroxide or alkaline earth metal hydroxide is slowly added while mixing to form HNB according to the following reaction scheme.

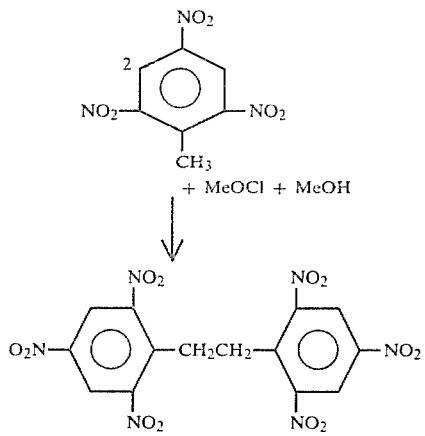

In the above reaction scheme MeOCl is a metal hypochlorite and MeOH is a metal hydroxide. The symbol Me denotes an alkali metal, such as sodium, potassium and lithium, or an alkaline-earth metal, such as strontium, calcium and barium. The solution of metal hypochlorite may be of any convenient concentration but dilute solutions of about 5% to about 15% by weight being readily available are preferred. Although the use of the alkali metal or alkaline-earth metal hypochlorite solution is preferred, organic reagents such as alkyl hypochlorite may be used in lieu thereof. An example of such compounds is tertiary butyl hypochlorite. To insure the correct reaction scheme, the pH of the hypochlorite solution is adjusted to about 11.0 to 12.0 and preferably to about 11.3 to 11.7 by adding an alkali metal or alkaline-earth metal hydroxide to the solution.

In accordance with the present invention, after the hypochlorite solution is added to the TNT solution the reaction proceeds immediately and the HNB can be filtered from the solution without delay. Alternatively, the reaction can be allowed to proceed for a suitable aging time. The temperature at which the reaction can proceed are from about 35° C. to about 75° C. and preferably from about 40° C. to about 65° C. The filtered HNB is then washed in methanol and dried. Yields of HNB as high as 70% of the theoretical yield and better can be thus obtained. This is in contrast to Shipp and Kaplan, who emphasize the desirability of using a reaction temperature under 15° C. to avoid harmful side reactions between TNT and alkali.

The following examples will more fully illustrate the embodiments of the invention. Unless otherwise specified, all parts and percentages are by weight.

EXAMPLE I

Following Example V of U.S. Pat. No. 3,505,413, 10 grams of TNT is dissolved in a solvent system comprising 50 mls of tetrahydrofuran (THF) and 100 mls of methanol. 100 mls of a b 1.8% sodium hypochlorite solution containing 0.5 gram of NaOH is added to the TNT solution over a period of 5 or 10 minutes in order to control the temperature so as not to exceed 35° C. The reaction mixture is allowed to stand for 15 minutes and the precipitate is then filtered from the solution, washed thoroughly with methanol and dried. The yield of HNB is 7.9 grams (79% of theoretical). When the Shipp, Kaplan process is repeated using acetonitrile as the co-solvent in place of the THF, the yield of HNB is 59% of theoretical. The materials obtained have a melting range of about 195° C. to 205° C. and are purple brown in color.

Shipp and Kaplan reported a melting range of 218° C. to 220° C. for recrystallized HNB. The material obtained in accordance with the present invention is light in color with melting ranges higher than that obtained in the prior art processes. Accordingly, a less crude product can be obtained with the present process.

EXAMPLE II 5 grams of TNT is dissolved in 300 mls of methanol at room temperature. 18 mls of a 5% sodium hypochlorite solution is added to 33 mls of water containing 0.25 gram of sodium hydroxide. The alkaline sodium hypochlorite solution is then added dropwise to the TNT solution over a 5 to 10 minute period while magnetically stirring the reaction mixture. The reaction temperature reaches but never exceeds 35° C. The reaction mixture is then stirred for 30 minutes and the precipitate formed is filtered from the solution. The precipitate is then washed thoroughly with methanol and dried to yield 2.2 grams (44% of theoretical) of HNB m.p. 209° C.-215° C. as determined by infrared spectrum.

EXAMPLE III 10 grams of TNT is dissolved in 100 mls of methanol at 60° C. The TNT solution is then cooled to 45° to 50° C. 35 mls of a 5% sodium hypochlorite aqueous solution containing 0.5 grams of sodium hydroxide is then added dropwise to the TNT solution over a 5 to 10 minute period while stirring. The temperature of the reaction mixture is maintained at about 50° C. The precipitate formed is then immediately filtered from the solution, washed with methanol and dried to yield 7.9 grams (79% of theoretical) of HNB having a melting range of 198° C. to 208° C.

EXAMPLE IV 5 grams of TNT is dissolved in 65 mls of methanol. 18 mls of a 5% sodium hypochlorite aqueous solution containing 0.25 grams of sodium hydroxide is then added dropwise to the TNT solution over a 5 to 10 minute period while stirring. The temperature of the reaction mixture is maintained at 40° C. The precipitate formed is then immediately filtered from the solution, washed with methanol and dried to yield 3.8 grams (76% of theoretical) of HNB.

EXAMPLE V 5 grams of TNT is dissolved in 50 mls of methanol. 14.5 mls of a 5% hypochlorite solution containing 0.2 grams of sodium hydroxide is added dropwise to the TNT solution over a 5 to 10 minute period while stirring. The temperature of the reaction mixture is maintained at about 60° C. The precipitate formed is then immediately filtered from the solution, washed with methanol and dried to yield 3.7 grams (74% of theoretical) of HNB.

EXAMPLE VI 5 grams of TNT is dissolved in 35 mls of methanol. 14.5 mls of a 5% hypochlorite solution containing 0.2 grams of sodium hydroxide is added dropwise to the TNT solution over a 5 to 10 minute period while stirring. The temperature of the reaction mixture is maintained at about 60° C. The precipitate formed is then immediately filtered, washed in methanol and dried to yield 3.6 grams (71% of theoretical) of HNB.

EXAMPLE VII 5 grams of TNT is dissolved in 25 mls of methanol. 18 mls of a 5% sodium hypochlorite solution containing 0.25 grams of sodium hydroxide is then added dropwise to the TNT solution over a 5 to 10 minute period while stirring. The reaction temperature is maintained at about 65° C. The precipitate formed is then immediately filtered from the solution, washed in methanol and dried to yield 3.3 grams (66% of theoretical) of HNB.

EXAMPLE VIII 5 grams of TNT is dissolved in 100 mls of a 97% ethanol solution. 22 mls of a 5% sodium hypochlorite solution containing 0.3 grams of sodium hydroxide is added dropwise to the TNT solution over a 5 to 10 minute period while stirring. The temperature of the reaction mixture is maintained at about 50° C. The precipitate formed is then immediately filtered from the solution, washed in methanol and dried to yield 3.9 grams (78% of theoretical) of HNB.

EXAMPLE IX 5 grams of TNT is dissolved in 25 mls of 2-methoxyethanol. 14.5 mls of a 5% sodium hypochlorite solution containing 0.2 grams of sodium hydroxide is added dropwise to the TNT solution over a 5 to 10 minute period while stirring. The temperature of the reaction mixture is maintained at about 50° C. The precipitate formed is then immediately filtered from the solution, washed in methanol and dried to yield 3.8 grams (76% of theoretical) of HNB.

EXAMPLE X

The process of Example VIII is repeated but 175 mls of isopropanol is used in place of the ethanol. The process produces 1.7 grams (34% of theoretical) of HNB.

EXAMPLE XI

The process of Example VII is repeated but 25 mls of acetone is used in place of the methanol. The process produces 1.4 grams (28% of theoretical) of HNB.

EXAMPLE XII

The process of Example VII is repeated but 75 mls of THF is used in place of the methanol. The process produces 1.7 grams (34% of theoretical) of HNB.

EXAMPLE XIII

The process of Example VII is repeated but 25 mls of N,N-dimethylformamide is used in place of the methanol. The process produces 3.2 grams (63% of theoretical) of HNB.

EXAMPLE XIV

The process of Example IX is repeated but 20 mls of N,N-dimethylacetamide is used in place of the 2-methoxyethanol. The process produces 3,4 grams (68% of theoretical) of HNB.

EXAMPLE XV

The process of Example VII is repeated but 25 mls of pyridine is used in place of the methanol. The process produces 2.2 grams (44% of theoretical) of HNB.

EXAMPLE XVI

The process of Example VII is repeated but 25 mls of N-methyl pyrrolidinone is used in place of the methanol. The process produced 2.7 grams (54% of theoretical) of HNB.

EXAMPLES XVII THROUGH XX

The process of Example VII is repeated but the following solvents are used in place of the methanol.

15 ml toluene
50 ml ethyl acetate
75 ml formamide

No HNB is produced with any of these solvents.

This invention has been described with respect to certain preferred embodiments and various modifications. Variations in the light thereof will be suggested to persons skilled in the art and are to be included within the spirit and purview of this application and the scope of the appended claims.

What is claimed is:

1. A process for preparing 2,2',4,4',6,6'-hexanitrobibenzyl comprising the steps of adding an aqueous solution of an alkali or alkaline-earth metal hypochlorite containing a alkali or alkaline-earth metal hydroxide to a solution of trinitrotoluene in a solvent selected from the group consisting of methanol, ethanol, 2-methoxyethanol, isopropanol, acetone, tetrahydrofuran, N,N-dimethylformamide, N,N-dimethylacetamide, pyridine and N-methyl pyrrolidinone and then recovering said hexanitrobibenzyl.

2. A process as defined in claim 1, wherein the solvent is methanol.

3. A process as defined in claim 1, wherein the reaction is carried out at temperatures of about 40° C. to 65° C.

4. A process as defined in claim 1, wherein from about 5 mls to about 20 mls of solvent is used for each gram of TNT.

5. A process as defined in claim 1, wherein the solvent is heated to temperatures from about 40° C. to about 70° C. to increase the solubility of TNT in said solvent.

6. A process as defined in claim 1 of claim 2, wherein the metal hypochlorite is sodium hypochlorite and the metal hydroxide is sodium hydroxide.

7. A process as defined in claim 1, wherein the hexanitrobibenzyl is immediately filtered from the reaction mixture upon completion of the addition of the hypochlorite solution to the TNT solution.

8. A process as defined in claim 1, wherein the solvent is ethanol.

9. A process as defined in claim 8, wherein the solvent is methoxyethanol.

* * * * *